US00PP08451P

United States Patent [19]

Jessel, Jr.

[11] Patent Number: Plant 8,451

[45] Date of Patent: Nov. 9, 1993

[54] CARNATION PLANT NAMED CFPC BROCADE

[76] Inventor: Walter H. Jessel, Jr., 128 W. Alvin Dr., Apt. C, Salinas, Calif. 93906

[21] Appl. No.: 950,472

[22] Filed: Sep. 24, 1992

[51] Int. Cl.[5] ..... A01H 5/00

[52] U.S. Cl. ..... Plt./70.2

[58] Field of Search ..... Plt./70.1, 70.2, 70.4

*Primary Examiner*—Howard J. Locker

*Attorney, Agent, or Firm*—Christie, Parker & Hale

[57] ABSTRACT

A new carnation of light yellow picotee purple coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC BROCADE'.

Among the novel combination of charactertistics possessed by the new variety which distinguishes it are light yellow picotee purple flowers which retain their coloration without fading. The plant is very vigorous, free-breaking with strong stems and of good disease resistance.

'CFPC Brocade' has 5 to 6 weeks faster flowering response, better spray formation and higher flower production than the variety, 'May Britt' which is no longer grown commercially. Also, the 'May Britt' flowers had a darker yellow background and darker purple picotee.

Asexual reproduction by propagation by side shoot cuttings of the new variety as performed in Fremont and Salinas, Calif, shows that the foregoing and other distinguishing characteristics come true to form and are established and transmitted through succeeding propagations. Although propagation by side shoot cuttings is described, other known methods of asexual reproduction may also be used to reproduce 'CFPC Brocade.'

BRIEF DESCRIPTION OF THE ILLUSTRATION

The accompanying illustration shows typical specimens of the vegetative growth and flowers in different stages of developemnt of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Brocade'.

Classification:

*Botanical.*—*Dianthus caryophyllus.*

*Commercial.*—Carnation, spray type.

Parentage:

*Female parent.*—Unnamed seedling (No. 870775).

'*Male parent.*—Unnamed seedling (No. 871000).

Plant:

*Height.*—About 32 inches.

*Growing Habit.*—Herbaceous, semi-upright, very vigorous, free breaking.

*Blooming Habit.*—Terminal as a spray.

*Blooming Season.*—Year round.

*Rooting Time.*—About 16 days.

*Mutation Prone.*—Does not appear to be.

*Disease Resistance.*—Good.

*Temperature Tolerance.*—Typical for carnation.

*Breaking Action.*—Very good.

Foliage:

*Color.*—Upper side: Near 139A. Lower side: Near 141A.

*Size.*—About 6 inches long at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1½ inches.

*Diameter.*—About ½-inch.

Calyx:

*Number of sepals.*—About 5.

*Length.*—About 1-inch.

*Width.*—About ⅓-inch.

*Color.*—Outside near 143A. Inside near 144D.

Bloom:

*Shape.*—Round.

*Size.*—Diameter average: About 2 inches. Depth average: About 1 inch.

*Borne.*—Terminal as a spray.

*Color.*—General tonality: Light yellow picotee purple, near 71B to 71C. Upper side: Near to from 12C to 12D. Lower side: Near 12D. Center: Near 12C, picotee near 80C faded.

*Keeping quality.*—Very good.
*Fragrance.*—Slight.

Petals:

*Number.*—About 25.
*Outer petals.*—Length: About 1-inch. Width: About 1-inch.
*Central petals.*—Length: About 1-inch.
*Width: About ½-inch.*
*Texture.*—Smooth.
*Form.*—Fan shaped.
*Appearance.*—Shiny.

Reproductive organs:

*Stamens.*—Number: About 10. Arrangement: Around the ovary.

*Anthers.*—Length: About 1/9-inch. Color: Near 161A.
*Filments.*—Length: About 1-inch. Color: Near 155B.
*Pistil.*—Number: About 3. Color: Near 155A.
*Stigma.*—Number: About 3. Color: Near 155A.
*Ovary.*—Shape: Conical. Color: Base — green. Body — green. Apex — tan.
*Fertility.*—Male — average. Female — average.

I claim:

1. A new and distinct variety of carnation plant, substantially as shown and described.

* * * * *

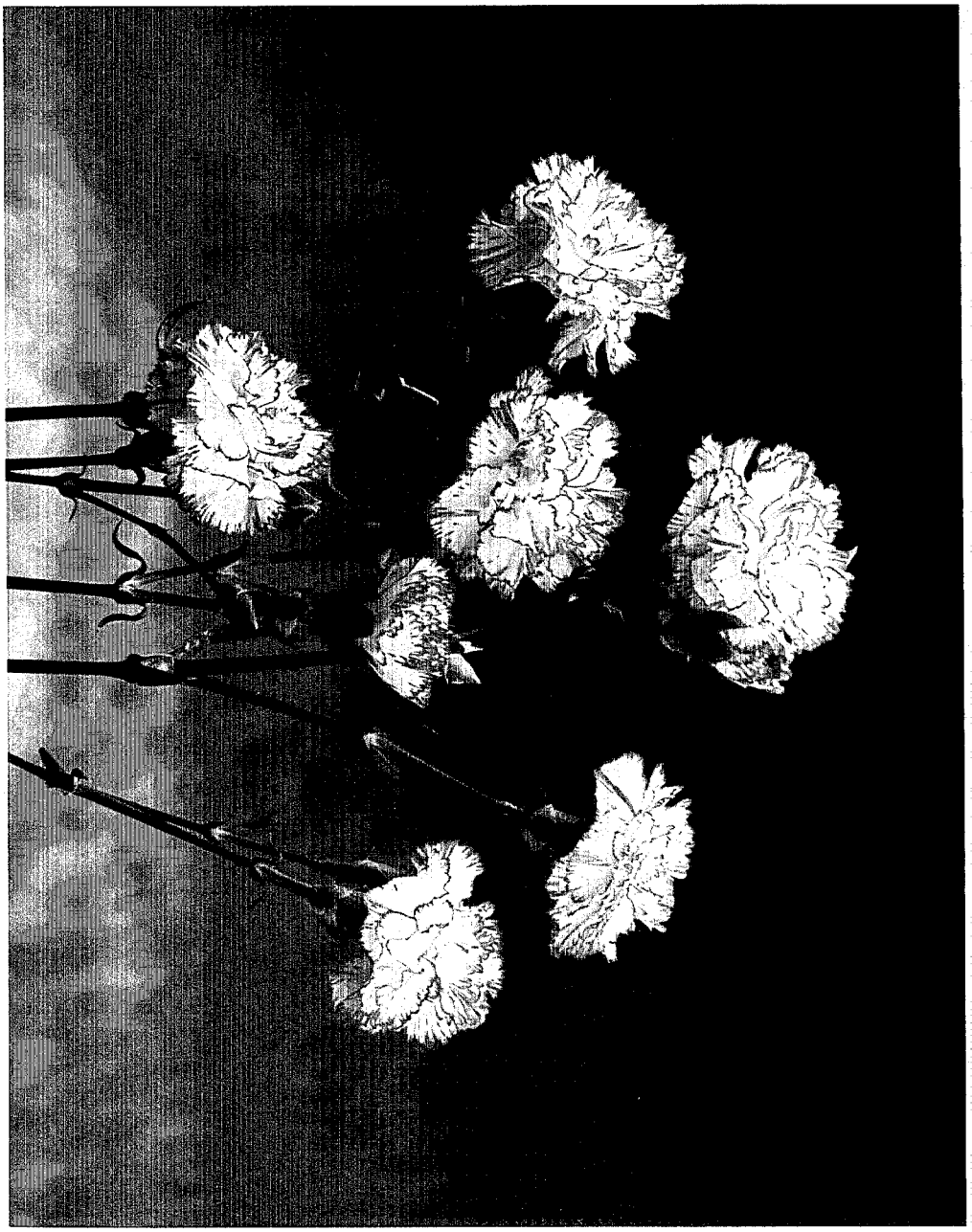

UNITED STATES PATENT AND TRADEMARK OFFICE

CERTIFICATE OF CORRECTION

PATENT NO. : Plant 8, 451
DATED : November 9, 1993
INVENTOR(S) : Walter H. Jessel, Jr.

It is certified that error appears in the above-indentified patent and that said Letters Patent is hereby corrected as shown below:

Column 1, lines 18, 19, change "'May Britt'" to -- 'Maj Britt' -- (both occurrences).

Column 1, line 34, change "developemnt" to -- development --.

Column 2, line 10, change "'Male parent." to -- Male parent. --.

Signed and Sealed this

Thirtieth Day of August, 1994

*Attest:*

*Attesting Officer*

Bruce Lehman

BRUCE LEHMAN

*Commissioner of Patents and Trademarks*

UNITED STATES PATENT AND TRADEMARK OFFICE

CERTIFICATE OF CORRECTION

PATENT NO. : Plant 8,451

DATED : November 9, 1993

INVENTOR(S) : Walter H. Jessel, Jr.

It is certified that error appears in the above-indentified patent and that said Letters Patent is hereby corrected as shown below:

On the Title Page:

Assignee omitted, insert the Assignee as follows:

-- [73] Assignee: California Florida Plant Co., L.P., Salinas, Calif. --

Column 1, lines 18,19, change "'May Britt'" to -- 'Maj Britt' -- (both occurrences).

Column 1, line 34, change "developemnt" to -- development --.

Column 2, line 10, change "'*Male parent*." to -- *Male parent*. --.

Signed and Sealed this

Eleventh Day of October, 1994

*Attest:*

*Attesting Officer*

BRUCE LEHMAN

*Commissioner of Patents and Trademarks*